(12) United States Patent
Mertens et al.

(10) Patent No.: US 6,696,032 B2
(45) Date of Patent: Feb. 24, 2004

(54) PROCESS FOR MANUFACTURING A SILICOALUMINOPHOSPHATE MOLECULAR SIEVE

(75) Inventors: Machteld Mertens, Boortmeerbeek (BE); Karl G. Strohmaier, Port Murray, NJ (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 0 days.

(21) Appl. No.: 09/997,779

(22) Filed: Nov. 29, 2001

(65) Prior Publication Data

US 2003/0104931 A1 Jun. 5, 2003

(51) Int. Cl.$^7$ ................................................ C01B 37/08
(52) U.S. Cl. ............................... 423/306; 423/DIG. 30; 502/214
(58) Field of Search ................... 423/716, 306, 423/DIG. 30; 502/214

(56) References Cited

U.S. PATENT DOCUMENTS

| | | | |
|---|---|---|---|
| 4,440,871 A | | 4/1984 | Lok et al. .................. 502/234 |
| 5,126,308 A | * | 6/1992 | Barger et al. ................ 502/214 |
| 5,279,810 A | * | 1/1994 | Calabro ....................... 423/701 |
| 5,663,471 A | * | 9/1997 | Kvisle et al. ................ 585/639 |
| 5,912,393 A | * | 6/1999 | Barger et al. ................ 585/640 |
| 6,207,872 B1 | * | 3/2001 | Barger et al. ................ 585/640 |

FOREIGN PATENT DOCUMENTS

| | | | | |
|---|---|---|---|---|
| EP | | 185525 A | 6/1986 | ........... C01B/33/28 |
| EP | | 541915 A | 11/1991 | ........... C07C/11/02 |
| WO | WO 00/06493 | | 2/2000 | ........... C01B/37/04 |
| WO | WO 01/36328 | | 5/2001 | ........... C01B/37/06 |

OTHER PUBLICATIONS

Dahl et al., *The Effect of Cyrstallite Size on the Activity and Selectivity of the Reaction of Ethanol and 2–Propanol Over SAPO–34, Microporous and Mesoporous Materials*, vol. 29, pp. 159–171 (1999).

Zu–gang et al., *Synthesis and Properties of SAPO–34 Catalyst for Endothermic Fuel, Journal of Propulsion Technology*, vol. 22, pp. 341–344, (2001).

Bhattacharya et al., Studies on the Synthesis of SAPO–5, J. Chem. Tech. Biotechnol., vol. 54, pp. 399–407, (1992).

* cited by examiner

Primary Examiner—David Sample

(57) ABSTRACT

Small particle size SAPO-34 is obtained by using a tetraalkyl orthosilicate as the silicon source.

15 Claims, No Drawings

PROCESS FOR MANUFACTURING A SILICOALUMINOPHOSPHATE MOLECULAR SIEVE

FIELD OF INVENTION

This invention relates to molecular sieves and processes for their manufacture. More especially it relates to the preparation of synthesis mixtures to control product characteristics. The invention relates especially to the manufacture of silicoaluminophosphate molecular sieves, and more especially SAPO-34.

BACKGROUND OF THE INVENTION

In U.S. Pat. No. 4,440,871, the preparation of a number of phosphorus-containing molecular sieves is described.

The patent particularly describes processes for the manufacture of numerous crystalline microporous silicoaluminophosphates (SAPO's) including SAPO-34, employing sources of silicon (e.g., a silica sol), aluminium (e.g., hydrated aluminium oxide), and phosphorus (e.g., orthophosphoric acid), and an organic template, for example tetraethylammonium hydroxide (TEAOH), isopropylamine (iPrNH$_2$) or di-n-propylamine (DPA). The patent, the disclosure of which is incorporated by reference herein, gives X-ray diffraction data for the SAPO's and describes their utilities in catalysis and absorption.

International Application WO 00/06493 describes obtaining phosphorus-containing molecular sieves of lower particle size and narrower size distribution by agitation, e.g., stirring or tumbling.

EP-A-541 915 is concerned with the conversion of methanol to olefins (MTO), especially light ($C_2$ to $C_4$) olefins, using an aluminophosphate crystalline molecular sieve catalyst. The specification describes the advantages of small particle size catalysts in MTO processes, and provides a process for facilitating the manufacture of a small particle size material by stirring the synthesis mixture, producing SAPO-34 of median particle diameters, expressed as a mass distribution, in the range of about 0.6 to 1.4 $\mu$m.

EP-A-185 525 describes a process in which SAPO-37 is manufactured using a two-phase synthesis mixture. In an example there are used an aqueous phase containing phosphoric acid, alumina, and tetraethyl and tetrapropyl ammonium hydroxides as organic templates, and an organic phase comprising tetraethyl orthosilicate in hexanol, a solvent immiscible with water.

International Application WO 01/36328 describes a process in which a SAPO-34 molecular sieve is manufactured in the form of isocrystalline spheroidal particles of from 0.5 to 30 $\mu$m diameter using an aqueous synthesis mixture comprising a template, sources of the elements essential to the structure of the sieve and an organic solvent miscible with water, the purpose of the solvent being to solubilize the source of the silicon in the aqueous synthesis mixture, and a surfactant as morphology modifying agent. The silicon source may be a tetraalkyl orthosilicate.

The spheroidal particles of SAPO-34 are said to have a textured surface formed by crystallites the width (largest dimension) of which is from about 0.05 to 2.5 $\mu$m, as determined by scanning election microscopy. Although it is stated that reducing the concentration of silicon in the synthesis mixture reduced the diameter of the spheroids, the product of the SAPO-34 examples is always spheroidal.

There remains a need, however, for a method whereby very small individual crystallites of SAPO-34 can be manufactured, as opposed to the clusters resulting from the process described in WO 01/36328.

It has now been found that by omitting the surfactant a SAPO-34 product in the form of individual crystallites of much reduced particle size may be obtained.

SUMMARY OF THE INVENTION

The present invention accordingly provides a process for the manufacture of a SAPO-34 crystalline molecular sieve which comprises forming a surfactant-free synthesis mixture containing sources of silicon, of aluminium, and of phosphorus, in proportions appropriate to the formation of SAPO-34, and a structure-directing agent, the source of silica being a tetraalkyl orthosilicate, and subjecting the synthesis mixture to hydrothermal treatment.

Advantageously, the molar ratio of silicon to aluminium, expressed as $SiO_2:Al_2O_3$, is at most 0.5:1, since molar ratios higher than 0.5:1 are believed to contribute to the formation of a spheroidal particle as described in WO 01/36328.

The invention also provides SAPO-34, the mean particle size of which is at most 400 nm, advantageously at most 200 nm, preferably at most 100 nm and most preferably at most 50 nm. The SAPO-34 is advantageously one obtainable by, and preferably is obtained by, the process of the invention. Mean particle size may be measured by inspection of scanning electron micrographs (SEM's), the largest dimension of each particle being taken. Alternatively, particle size measurement may be carried out by XRD peak width analysis as described in certain of the Examples below.

DETAILED DESCRIPTION OF THE INVENTION

The components of the synthesis mixture used in the present invention are typically those known in the art or as described in the literature as suitable for the production of SAPO-34, as are the conditions of the hydrothermal treatment, except for the essential use of a tetraalkyl orthosilicate as the silicon source, the absence of surfactant and/or the required ratio of $Al_2O_3:SiO_2$. (It may be noted that while U.S. Pat. No. 4,440,871 mentions the possibility of using a tetraalkyl silicate as silicon source, none of its many examples does so.)

Although the synthesis mixture is surfactant-free, it is within the scope of the invention to incorporate an organic solvent miscible with water, other than a surfactant, that assists in solubilizing the tetraalkyl orthosilicate in the aqueous synthesis mixture. As organic solvent there may be mentioned sulphoxides and $C_1$ to $C_5$ oxygenated hydrocarbons, the latter advantageously being an acid, aldehyde, ketone or mono- or polyhydric alcohol. As examples there may be mentioned ethylene glycol, 1,2- and 1,3-propanediols, acetone, methanol, n- and isopropanol, butanol and, preferably, ethanol.

In general, the treatment of the synthesis mixture to yield the desired crystalline molecular sieve, usually termed hydrothermal treatment, is advantageously carried out under autogenous pressure, for example in an autoclave, for example a stainless steel autoclave which may, if desired, be preferably lined. The treatment may, for example, be carried out at a temperature within the range of from 50, advantageously from 90, especially 120, to 250° C., depending on the molecular sieve being made. The treatment may, for example, be carried out for a period within the range of from 1 to 200 hours, preferably up to 100 hours, again depending on the molecular sieve being formed. The procedure may include an ageing period, either at room temperature or, preferably, at a moderately elevated temperature, before the hydrothermal treatment at more elevated temperature. The latter may include a period of gradual or stepwise variation in temperature.

As source for the phosphorus in the synthesis mixture, there may be mentioned phosphoric acid, organic phosphates, e.g., triethylphosphate, and aluminophosphates.

As source for aluminium in the synthesis mixture there may be mentioned alumina hydrate, alumina, sodium aluminate, pseudoboehmite, aluminium phosphate, organic aluminium sources, e.g., alkoxides, for example, aluminium isopropoxide.

As source for silicon there may be mentioned, as indicated above, a tetraalkyl orthosilicate. There may be used, for example, tetramethyl orthosilicate, tetraethyl orthosilicate, tetrapropyl orthosilicate, and tetrabutyl orthosilicate. Tetraethyl orthosilicate (TEOS) is preferred.

In addition, the synthesis mixture will contain an organic structure-directing agent (template). In general, as indicated above, these compounds are generally organic bases, especially amines and quaternary ammonium compounds, used either singly or in mixtures.

As templates there may be mentioned, for example, tetraethyl ammonium hydroxide (TEAOH) and salts, e.g., phosphate, fluoride, chloride, bromide and acetate, dipropylamine (DPA), triethylamine, cyclohexylamine, 1-methylamidazole, morpholine, pyridine, piperidine, and diethylethanolamine (DEA).

The treatment may be carried out with the vessel static or, preferably, with stirring or with rotating the vessel about a horizontal axis (tumbling). If desired, the synthesis mixture may be stirred or tumbled during an initial part of the heating stage, for example, from room temperature to an elevated, e.g., the final treatment, temperature, and be static for the remainder. Agitation generally produces a product with a smaller particle size and a narrower particle size distribution than static hydrothermal treatment.

A synthesis mixture for producing SAPO-34 according to the invention advantageously has a molar composition, within the following ranges:

| | |
|---|---|
| $P_2O_5:Al_2O_3$ | 0.6 to 1.2:1, preferably about 1:1 |
| $SiO_2:Al_2O_3$ | 0.01 to 0.5:1, preferably 0.1 to 0.5:1 |
| $H_2O:Al_2O_3$ | 10 to 100:1 | together with an organic template, advantageously tetraethylammonium hydroxide (TEAOH), dipropylamine (DPA), isopropylamine or morpholine, or a mixture of two or more such templates, in a proportion appropriate to yield SAPO-34.

The present invention also provides the use in the manufacture of SAPO-34 by hydrothermal treatment of a synthesis mixture comprising sources of silicon, aluminium and phosphorus, of a tetraalkyl orthosilicate as silicon source to control the particle size of the product.

The invention further provides the products of the processes and of the uses of the earlier aspects of the invention. The products, if required after cation exchange and/or calcining, have utility as catalyst precursors, catalysts, and separation and absorption media. They are especially useful in numerous hydrocarbon conversions, separations and absorptions. They may be used alone, or in admixture with other molecular sieves, in particulate form, supported or unsupported, or in the form of a supported layer, for example in the form of a membrane, for example as described in International Application WO 94/25151. Hydrocarbon conversions include, for example, cracking, reforming, hydrofining, aromatization, oligomerisation, isomerization, dewaxing, and hydrocracking (e.g., naphtha to light olefins, higher to lower molecular weight hydrocarbons, alkylation, transalkylation, disproportionation or isomerization of aromatics). Other conversions include the reaction of alcohols with olefins and the conversion of oxygenates to hydrocarbons, especially of methanol to olefins, especially light olefins. SAPO-34 produced by the process of the invention is especially suitable for this conversion.

Conversion of oxygenates may be carried out with the oxygenate, e.g., methanol, in the liquid or, preferably, the vapour phase, in batch or, preferably, continuous mode. When carried out in continuous mode, a weight hourly space velocity (WHSV), based on oxygenate, of advantageously 1 to 1000, preferably 1 to 100, hour$^{-1}$ may conveniently be used. An elevated temperature is generally required to obtain economic conversion rates, e.g., one between 300 and 600° C., preferably from 400 to 500° C., and more preferably about 450° C. The catalyst may be in a fixed bed, or a dynamic, e.g., fluidized or moving, bed.

The oxygenate feedstock may be mixed with a diluent, inert under the reaction conditions, e.g., argon, nitrogen, carbon dioxide, hydrogen, or steam. The concentration of methanol in the feedstream may vary widely, e.g., from 5 to 90 mole per cent of the feedstock. The pressure may vary within a wide range, e.g., from atmospheric to 500 kPa.

EXAMPLES

The following Examples, in which parts are by weight unless otherwise indicated, illustrate the invention. The source and purity of starting materials are those first given, unless indicated otherwise.

Example 1

This example illustrates the manufacture of SAPO-34 using the process of the invention.

A synthesis mixture was prepared as follows:

9.75 parts of $H_3PO_4$ (85%), 9.70 parts of deionized water, and 5.84 parts of alumina hydrate (Catapal, Vista, 74% $Al_2O_3$, 26% $H_2O$) were mixed together. Then 35.6 parts of TEAOH (35% in water) were added and mixed in. Finally 15.6 parts of ethanol and 3.5 parts of TEOS were mixed in, to yield a synthesis mixture of molar composition:

$Al_2O_3:P_2O_5:0.4\ SiO_2:2\ TEAOH:50\ H_2O:8\ C_2H_5OH$

The synthesis mixture was placed in a preferably lined stainless steel autoclave, which was mounted on a shelf in an air oven, the shelf being rotated, tumbling the autoclave, and maintained at 200° C. for 24 hours. After cooling, the product was recovered by centrifuging, washed with water, and dried in an air oven. The powder X-ray diffraction (XRD) pattern showed the product to be SAPO-34 with some minor SAPO-18 intergrowth. The relatively broad diffraction peaks indicated a small crystal size.

Elemental analysis: Si, 3.72%: Al, 17.67%; P, 16.85%, representing a product stoichiometry of $Si_{0.100}Al_{0.492}P_{0.409}$.

Analysis of the peak widths of the XRD pattern and application of the Scherrer equation, correcting for the peak broadening caused by the instrument and the intergrowths, gave a mean crystal size of about 50 nm.

Example 2

In a procedure similar to that of Example 1, a synthesis mixture was prepared of molar composition:

$Al_2O_3:P_2O_5:0.3\ SiO_2:2\ TEAOH:40\ H_2O:8\ C_2H_5OH$

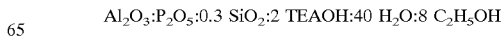

The synthesis mixture was placed in a preferably lined stainless steel autoclave, mounted on a shelf in an air oven, the shelf being rotated, and maintained at 200° C. for 24.5 hours. Recovery was carried out as in Example 1. The product was SAPO-34 with some minor SAPO-18 intergrowth. SEM analysis showed crystal size to be less than 0.1 μm, and analysis of the XRD pattern peak width and use of the Scherrer equation gave a mean crystal size of about 36 nm.

| Elemental analysis: | Si, 3.40%; Al, 17.4%; P, 16.4% |
|---|---|
| Stoichiometry | $Si_{0.093} Al_{0.498} P_{0.409}$ |

Example 3

Following the procedure of Example 1, there was prepared a synthesis mixture of molar composition:

$Al_2O_3:P_2O_5:0.3\ SiO_2:1.52\ TEAOH:30\ H_2O:16\ C_2H_5OH$

Hydrothermal treatment (200° C., 24.5 hours) and recovery were carried out as described in Example 2. The product was SAPO-34 with some minor SAPO-18 intergrowth. The relatively large width of the XRD pattern peaks indicated small crystal size, SEM analysis indicated a mean particle size of about 0.1 μm.

| Elemental analysis: | Si, 3.51%; Al, 17.4%; P 16.5% |
|---|---|
| Stoichiometry: | $Si_{0.096} Al_{0.495} P_{0.416}$ |

Example 4

148.9 parts $Al_2O_3$ (Condea Pural SB) were mixed with 590.9 parts of water, and 252.4 parts of $H_3PO_4$ (85%, Acros) together with 69.8 parts of TEOS were then added. 460.5 parts of TEAOH (35% in water, Eastern Chemical) together with 177.3 parts of DPA (Fluka) were then added, with continuous stirring to yield a synthesis mixture of molar composition:

$Al_2O_3: P_2O_5:0.3\ SiO_2:TEAOH:1.6\ DPA:52H_2O$

The synthesis mixture was placed in a stainless steel autoclave, heated over the course of 8 hours to 175° C. and maintained at that temperature with stirring at 170 rpm (tip speed of 0.89 m/s) for 48 hours. After recovery and analysis, the product was found to be pure SAPO-34. 50% by number of the crystals were of particle size less than 280 nm; 10% were of particle size greater than 400 nm. In comparison, using as silica source Ludox AS40, a 40% colloidal silica solution, instead of TEOS, in a synthesis mixture of the same molar composition and the same reaction conditions gave a pure SAPO-34 product of particle size about 1 μm.

Example 5

19.8 parts of $H_3PO_4$ (85%), 30 parts water, 5.4 parts TEOS, 11.9 parts alumina hydrate (Catapal), 72.3 parts TEAOH (35%), and 20.7 parts water were mixed in the order stated to give a synthesis mixture of the following molecular proportions:

$Al_2O_3:P_2O_5:0.3\ SiO_2:2\ TEAOH:70\ H_2O$

After homogenization in a blender, the synthesis mixture was placed in a preferably lined stainless steel autoclave, mounted for tumbling in an oven, and maintained at 200° C. for 24 hours. After cooling, the product was recovered by centrifuging, washed with water, and dried at 115° C. The XRD pattern showed the product to be pure SAPO-34, SEM showing cubic and thick platelet crystals of size ranging between 50 and 200 nm.

What is claimed is:

1. A process for the manufacture of a SAPO-34 crystalline molecular sieve, the process comprising the steps of: (a) forming a surfactant-free synthesis mixture containing sources of silicon, of aluminium, and of phosphorus, in proportions appropriate to the formation of SAPO-34, and a structure-directing agent, where the source of silicon is a tetraakyl orthosilicate, and (b) subjecting the synthesis mixture to hydrothermal treatment; wherein the SAPO-34 crystalline molecular sieve has a mean particle size of at most 400 nm.

2. The process of claim 1 wherein the synthesis mixture has a molar ratio of silicon to aluminium, expressed as $SiO_2:Al_2O_3$, of at most 0.5:1.

3. The process of claim 1 wherein the tetraalkyl orthosilicate is a tetraethyl orthosilicate.

4. The process of claim 1 wherein the tetraalkyl orthosilicate is selected from the group consisting of a tetramethyl orthosilicate, a tetrapropyl orthosilicate, and a tetrabutyl orthosilicate.

5. The process of claim 1 wherein the structure-directing agent is TEAOH or a mixture of TEAOH and DPA.

6. The process of claim 1 wherein at least apart of the hydrothermal treatment step is carried out with agitation.

7. The process of claim 1, wherein the synthesis mixture has a molar composition within the ranges of

| $P_2O_5:Al_2O_3$ | 0.6 to 1.2:1 |
|---|---|
| $SiO_2:Al_2O_3$ | 0.01 to 0.5:1 |
| $H_2O:Al_2O_3$ | 10 to 100:1 | together with the structure-directing agent.

8. The process of claim 1 wherein the SAPO-34 crystalline molecular sieve is subjected to the step(s) of one or more of the group consisting of washing, cation exchange, and calcining.

9. A SAPO-34 crystalline molecular sieve having a mean particle size of at most 200 nm.

10. The SAPO-34 crystalline molecular sieve of claim 9, wherein the mean particle size is at most 50 nm.

11. The SAPO-34 crystalline molecular sieve of claim 9, wherein the mean particle size is at most 100 nm.

12. A cation exchanged SAPO-34 crystalline molecular sieve having a mean particle size of at most 200 nm.

13. The SAPO-34 crystalline molecular sieve of claim 12, wherein the mean particle size is at most 100 nm.

14. The SAPO-34 crystalline molecular sieve of claim 12, wherein the mean particle size is at most 50 nm.

15. A process for the manufacture of a SAPO-34 crystalline molecular sieve, the process comprising the steps of: (a) forming a surfactant-free synthesis mixture comprising a source of silicon comprising tetraalkyl orthosilicate, a source of aluminium, and a source of phosphorus, in proportions appropriate to the formation of SAPO-34, and a structure-directing agent selected from the group consisting of TEAOH, DPA and mixtures thereof; and (b) subjecting the synthesis mixture to hydrothermal treatment.

* * * * *